(12) United States Patent
Sudhir et al.

(10) Patent No.: US 9,408,952 B2
(45) Date of Patent: Aug. 9, 2016

(54) PEDIATRIC APPLICATION OF BIOABSORBABLE POLYMER STENTS IN INFANTS AND CHILDREN WITH CONGENITAL HEART DEFECTS

(75) Inventors: Krishnankutty Sudhir, Santa Clara, CA (US); Wai-Fung Cheong, Los Altos, CA (US); Virginia Giddings, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 93 days.

(21) Appl. No.: 13/308,256

(22) Filed: Nov. 30, 2011

(65) Prior Publication Data

US 2013/0138206 A1 May 30, 2013

(51) Int. Cl.

| | |
|---|---|
| A61F 2/06 | (2013.01) |
| A61F 2/90 | (2013.01) |
| A61L 31/14 | (2006.01) |
| A61F 2/82 | (2013.01) |
| A61F 2/958 | (2013.01) |
| A61F 2/962 | (2013.01) |
| A61L 31/16 | (2006.01) |
| A61F 2/966 | (2013.01) |
| A61L 31/06 | (2006.01) |
| A61F 2/04 | (2013.01) |
| A61F 2/91 | (2013.01) |

(52) U.S. Cl.
CPC ............... *A61L 31/148* (2013.01); *A61F 2/82* (2013.01); *A61F 2/958* (2013.01); *A61F 2/962* (2013.01); *A61F 2/966* (2013.01); *A61L 31/06* (2013.01); *A61L 31/16* (2013.01); *A61F 2/04* (2013.01); *A61F 2/91* (2013.01); *A61F 2210/0004* (2013.01); *A61F 2250/009* (2013.01); *A61F 2250/0059* (2013.01); *A61F 2250/0082* (2013.01)

(58) Field of Classification Search
CPC . A61F 2210/0004; A61F 2/06; A61L 31/148; A61L 27/58; A61L 2400/00; A61L 2300/80
USPC .......................................................... 623/1.38
See application file for complete search history.

(56) References Cited

U.S. PATENT DOCUMENTS

| | | | |
|---|---|---|---|
| 5,766,237 A * | 6/1998 | Cragg | 606/194 |
| 5,792,106 A * | 8/1998 | Mische | 604/103.01 |
| 5,981,619 A * | 11/1999 | Shikinami et al. | 523/113 |
| 7,008,446 B1 * | 3/2006 | Amis et al. | 623/1.21 |
| 7,166,680 B2 * | 1/2007 | DesNoyer et al. | 525/425 |
| 2001/0021871 A1 * | 9/2001 | Stinson | 623/1.15 |
| 2002/0188342 A1 * | 12/2002 | Rykhus et al. | 623/1.2 |
| 2003/0069629 A1 * | 4/2003 | Jadhav et al. | 623/1.15 |
| 2003/0074049 A1 | 4/2003 | Hoganson | |
| 2003/0118692 A1 | 6/2003 | Wang | |
| 2004/0138738 A1 | 7/2004 | Stinson | |

(Continued)

OTHER PUBLICATIONS

Mayo Clinic Staff, Coarctation of the aorta, (Apr. 2012), Mayo Foundation for Medical Education and Research, pp. 1-5.*

(Continued)

*Primary Examiner* — Paul Prebilic
(74) *Attorney, Agent, or Firm* — Squire Patton Boggs (US) LLP (57) ABSTRACT

Methods of treating congenital heart defects in infants and children with bioabsorbable polymer stents are described. The treatments reduce or eliminate the adverse affects of congenital heart defects or may be palliative.

10 Claims, 2 Drawing Sheets

(56) References Cited

U.S. PATENT DOCUMENTS

| | | | | |
|---|---|---|---|---|
| 2005/0049674 A1* | 3/2005 | Berra et al. | | 623/1.13 |
| 2005/0119733 A1* | 6/2005 | Wiliams et al. | | 623/1.49 |
| 2006/0020324 A1* | 1/2006 | Schmid et al. | | 623/1.16 |
| 2006/0026815 A1* | 2/2006 | Padilla et al. | | 29/558 |
| 2006/0064160 A1* | 3/2006 | Gerold et al. | | 623/1.38 |
| 2006/0085065 A1* | 4/2006 | Krause et al. | | 623/1.44 |
| 2006/0161241 A1* | 7/2006 | Barbut et al. | | 623/1.15 |
| 2007/0162110 A1* | 7/2007 | Dave | | 623/1.42 |
| 2007/0198078 A1* | 8/2007 | Berra et al. | | 623/1.12 |
| 2007/0276465 A1* | 11/2007 | Mongrain et al. | | 623/1.15 |
| 2007/0282431 A1* | 12/2007 | Gale et al. | | 623/1.38 |
| 2007/0283552 A1 | 12/2007 | Gale et al. | | |
| 2008/0051882 A1 | 2/2008 | Rubin | | |
| 2008/0140179 A1 | 6/2008 | Ladisa | | |
| 2008/0275537 A1 | 11/2008 | Limon | | |
| 2009/0099644 A1* | 4/2009 | Biadillah et al. | | 623/1.16 |
| 2010/0004735 A1 | 1/2010 | Yang et al. | | |
| 2010/0042202 A1 | 2/2010 | Ramzipoor | | |
| 2010/0130447 A1 | 5/2010 | Burns | | |
| 2010/0262224 A1* | 10/2010 | Kleiner | | 623/1.15 |
| 2012/0290070 A1* | 11/2012 | Wang et al. | | 623/1.15 |

OTHER PUBLICATIONS

"Cardiovascular Replacement Therapy in Children", downloaded www.biomed.brown.edu/Courses/BI108/BI108_2008Groups/group09/page%205.html, Jun. 28, 2011, 4 pgs.

Baum et al., "Congenital Stenosis of the Pulmonary Artery Branches", Circulation 29, pp. 680-687 (May 1964).

Kreutzer et al., "Isolated Peripheral Pulmonary Artery Stenoses in the Adult", Circulation 93, pp. 1417-1423 (Apr. 1996).

Ormiston et al., "A bioabsorbable everolimus-eluting coronary stent system for patients with single de-novo coronary artery lesions (ABSORB): a prospective open-label trial", The Lancet 371, pp. 899-907. (Mar. 2008).

Ormiston et al., "Bioabsorbable Coronary Stents", Circ. Cardiovasc. Interv. 2, pp. 255-260 (Jun. 2009).

Peters et al., "The role of stents in the treatment of congenital heart disease: Current status and future perspectives" Ann. Pediatr. Cardiol. 2(1) pp. 3-23 (Jun. 2009).

Ruiz et al., "Stenting the Ductus Arteriosus A "Wanna-Be" Blalock-Taussig", Circulation 99, pp. 2608-2609 (1999), (May 2009).

Serruys et al., "A bioabsorbable everolimus-eluting coronary stent system (ABSORB): 2-year outcomes and results from multiple imaging methods", The Lancet 373, pp. 897-910 (Mar. 2009).

Zartner et al., "First successful implantation of a biodegradable metal stent into the left pulmonary artery of a preterm baby", Catheter Cardiovasc. Interv. 66, pp. 595-596 (Dec. 2005) Abstract 1 pg.

Saito et al., "New tubular Bioabsorbable Knitted Airway Stent: Feasibility Assessment for Delivery and Deployment in a Dog Model", Am. Thorac. Surg. 78, pp. 1438-1440 (2004). Abstract 7 pgs, Oct. 2004.

NIH publication, "What is Tetralogy of Fallot?" Jul. 1, 2011, 2 pp.

NIH publication "What is Patent Ductus Arteriosus?" Sep. 26, 2011, 1 pp.

* cited by examiner

PEDIATRIC APPLICATION OF BIOABSORBABLE POLYMER STENTS IN INFANTS AND CHILDREN WITH CONGENITAL HEART DEFECTS

BACKGROUND OF THE INVENTION

1. Field of the Invention

This invention relates to methods of treatment relating to pediatric application of bioabsorbable polymer stents.

2. Description of the State of the Art

This invention relates generally to methods of treatment with radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be have sufficient radial strength so that it is capable of withstanding the structural loads, namely radial compressive forces imposed on the stent as it supports the walls of a vessel. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-degradable materials, such as metals, have become the standard of care for percutaneous coronary intervention (PCI) as well as in peripheral applications, such as the superficial femoral artery (SFA), since such stents have been shown to be capable of preventing early and later recoil and restenosis.

In order to effect healing of a diseased blood vessel, the presence of the stent is necessary only for a limited period of time, as the artery undergoes physiological remodeling over time. The development of a bioabsorbable stent or scaffold could obviate the permanent metal implant in vessel, allow late expansive luminal and vessel remodeling, and leave only healed native vessel tissue after the full absorption of the scaffold. Stents fabricated from bioresorbable, biodegradable, bioabsorbable, and/or bioerodable materials such as bioabsorbable polymers can be designed to completely absorb only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, provide the potential for plaque regression.

Intravascular or intracardiac stenoses occur in many forms of congenital heart disease (CHD). Therefore, the implantation of stents has become an accepted interventional procedure for stenotic lesions in pediatric cardiology. Despite the tremendous technical improvements over the last 20 years, the "ideal stent" has not yet been developed. Currently available stents have their advantages and disadvantages for common application in CHD's. One disadvantage of stents made of durable materials is the failure to adapt to somatic growth, i.e., after implantation in a vessel in a pediatric patient, the vessel grows resulting in a size mismatch between the stent and the vessel. A permanent stent also complicates later reintervention with a stent or surgery.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a method of treating a congenital heart defect in a human patient comprising: identifying one or more segments that are narrowed in one or more peripheral branches of the pulmonary artery of a human child; deploying one or more bioabsorbable polymer scaffolds in one or more of the narrowed segments, wherein the deployed bioabsorbable scaffolds provide support at the segments at an increased diameter to allow increased blood flow which facilitates development of the lungs of the human patient for a period of at least 6 months, wherein the deployed scaffolds eventually completely absorb away.

Additional embodiments of the present invention include a method of treating a congenital heart defect in a human patient comprising: identifying a human child having abnormalities associated with Tetralogy of the Fallot, wherein the abnormalities include pulmonary stenosis and at least two additional abnormalities from the group consisting of ventricular septal defect, right ventricular hypertrophy and overriding of the aorta; deploying a bioabsorbable polymer scaffold in the pulmonary artery of the patient, wherein the deployed bioabsorbable scaffold provides support at an increased diameter to allow increased blood flow into the lung of the patient, wherein the increased blood flow facilitates development of the lungs; performing surgical repair of at least one of the additional abnormalities at some time after deployment, wherein the scaffold is completely absorbed after providing the support for a period of time.

Other embodiments of the present invention include a method of treating a congenital heart defect in a human patient comprising: identifying a newborn human patient having a complex congenital cardiac malformation; and deploying a bioabsorbable polymer scaffold in the ductus arteriosis of the patient to maintain patency of the ductus arteriosis, wherein the patency of the ductus arteriosis allows blood flow to the lungs and the body until the complex congenital cardiac malformation is repaired, and wherein the scaffold is completely absorbed from the segment after providing the patency for a period of time.

Further embodiments of the present invention include a method of treating a coarctation of the aorta in a human patient comprising: identifying a narrowed segment in the aorta of a human child, wherein the aorta narrows in an area where the ductus arteriosus inserts in the aorta; deploying a bioabsorbable polymer scaffold at the narrowed segment, wherein the deployed bioabsorbable scaffold provides support at the segment at an increased diameter, wherein the deployed scaffold eventually completely absorbs away.

DETAILED DESCRIPTION OF THE INVENTION

Various embodiments of the present invention include treatment of congenital heart defects in human infants and children with bioabsorbable polymer stents. A human infant or child refers to a human patient less than 12 months old, 12 months to 2 years old, 2 to 3 years old, 3 to 5 years old, or greater than 5 years old. A newborn can refer to a human patient less than 1 day old, 1 day to 1 week old, or 1 to 2 weeks old. The treatment with the stents may reduce or eliminate the adverse affects of congenital heart defects or may be palliative. In the latter case, palliative refers to relieving or soothing the symptoms of the CHD to allow intervention that corrects defects of the CHD at a later time that is safer for the patient.

The embodiments of the invention include treatments of CHD's including peripheral pulmonary artery stenosis, tetralogy of fallot, cardiac conditions that require patency of the ductus arteriosus, and coarcation of aorta.

Peripheral pulmonary artery stenosis (PPS) in children is characterized by diffuse arterial involvement generally affecting the main and lobar arteries and occasionally produces symptoms of right ventricular (RV) failure when severe. Circulation 1996; 93:1417-1423. In general, congenital stenosis of the pulmonary artery branches is an anomaly characterized by narrowed segments of one or more of the main or peripheral branches of the pulmonary artery. Circulation 1964, 29:680-687. The disease has been treated by angioplasty and stenting to keep these arteries open and allow normal lung development.

Tetralogy of Fallot is a congenital heart defect which is classically understood to involve four anatomical abnormalities (although only three of them are always present). These four abnormalities are pulmonary stenosis, ventricular septal defect, right ventricular hypertrophy and overriding of the aorta. It is the most common cyanotic heart defect, and the most common cause of blue baby syndrome. Untreated, Tetralogy of Fallot rapidly results in progressive right ventricular hypertrophy due to the increased resistance on the right ventricle. This progresses to heart failure (dilated cardiomyopathy) which begins in the right heart and often leads to left heart failure. Angioplasty and stenting with permanent stents of the main pulmonary artery through the right ventricular outflow tract have been attempted with some success prior to definitive corrective surgery.

In the developing fetus, the ductus arteriosus (DA), also called the ductus Botalli, is a shunt connecting the pulmonary artery to the aortic arch. It allows most of the blood from the right ventricle to bypass the fetus's fluid-filled lungs. There are two other fetal shunts, the ductus venosus and the foramen ovale.

Permanent stents have been used to maintain the patency of the ductus arteriosus as a palliative treatment in neonates with ductal-dependent systemic blood flow and infants with ductal-dependent pulmonary blood flow congenital anomalies. Circulation 1999; 99:2608-2609. Anomalies include complex congenital cardiac malformation that is present in the first year of life. Such malformations include single ventricle with pulmonary atresia, hypoplastic left-heart syndrome and transposition of great vessels. These conditions are associated with very high infant mortality rates. Current treatment is neonatal transplantation, however, patency of the ductus arteriosus must be maintained until a suitable donor organ can be found. Thus maintaining the patency of the ductus is critical.

A child with a single ventricle defect is born with a heart with only one ventricle that is large enough or strong enough to pump effectively. Single ventricle defects include hypoplastic left heart syndrome, tricuspid atresia, double inlet left ventricle, and others. Hypoplastic left heart syndrome occurs when parts of the left side of the heart (mitral valve, left ventricle aortic valve, and aorta) do not develop completely. The condition is congenital. Transposition of the great vessels (TGV) is a group of congenital heart defects (CHDs) involving an abnormal spatial arrangement of any of the primary blood vessels: superior and/or inferior vena cavae (SVC, IVC), pulmonary artery, pulmonary veins, and aorta. CHDs involving only the primary arteries (pulmonary artery and aorta) belong to a sub-group called transposition of the great arteries (TGA). Typically, these patients are: neonates or less than 1 year old who are moribund and have high death rates.

Coarctation of the aorta, or aortic coarctation, is a congenital condition whereby the aorta narrows in the area where the ductus arteriosus (ligamentum arteriosum after regression) inserts. There are three types.

The first is preductal coarctation in which the narrowing is proximal to the ductus arteriosus. Blood flow to the aorta that is distal to the narrowing is dependent on the ductus arteriosus; therefore severe coarctation can be life-threatening. Preductal coarctation results when an intracardiac anomaly during fetal life decreases blood flow through the left side of the heart, leading to hypoplastic development of the aorta. This is the type seen in approximately 5% of infants with Turner Syndrome.

The second is ductal coarctation in which the narrowing occurs at the insertion of the ductus arteriosus. This kind usually appears when the ductus arteriosus closes.

The third is postductal coarctation in which the narrowing is distal to the insertion of the ductus arteriosus. Even with an open ductus arteriosus blood flow to the lower body can be impaired. This type is most common in adults. It is associated with notching of the ribs (because of collateral circulation), hypertension in the upper extremities, and weak pulses in the lower extremities. Postductal coarctation is most likely the result of the extension of a muscular artery (ductus arteriosus) into an elastic artery (aorta) during fetal life, where the contraction and fibrosis of the ductus arteriosus upon birth subsequently narrows the aortic lumen.

The treatment of CHD's with stents has been limited (with exceptions noted herein) to permanent or biostable metallic stents. However, permanent metallic stenting is sub-optimal because of continued growth of the child. This may lead to the need for redilation of the stent and restenosis. As mentioned above, the vessel growth results in a size mismatch between the stent and the vessel.

The use of bioabsorbable polymer stents has a number of advantages. (i) The stent disappears from the treated site resulting in reduction or elimination of late stent thrombosis. (ii) Disappearance of the stent facilitates repeat treatments (surgical or percutaneous) to the same site. (iii) Disappearance of the stent allows restoration of vasomotion at the treatment site. The presence of a rigid permanent metal stent restricts vasomotion. (iv) The bioabsorbability results in freedom from side-branch obstruction by struts. (v) The disappearance results in freedom from strut fracture and ensuing restenosis. The progression of stenosis seen within stents 7 to 10 years after stenting has been attributed, at least in part, to inflammation around metallic struts.

With respect to pediatric application of bioabsorbable stents, since a bioabsorbable stent disappears, vascular growth and development of the patient is accommodated. The BVS bioresorbable polymer stents has been applied to the coronary artery in adults. (Abbott Laboratories, Abbott Park, Ill., USA) made from poly(L-lactide) (PLLA) has undergone two sets of clinical trials. The studies have demonstrated feasibility for treatment of stenosis in coronary arteries. Circulation: Cardiovascular Interventions, 2009; 2: 255-260, The Lancet, Volume 371, Issue 9616, Pages 899-907, 15 Mar. 2008, The Lancet, Volume 373, Issue 9667, Pages 897-910, 14 March 200.

Corrodible metal stents using magnesium alloys have been tested in several trials in coronary arteries. Lancet 2007; 369:1869-75; J Endovasc Ther. 2005; 12:1-5; news-medical-.net BIOSOLVE-I, May 19, 2011. For pediatric applications, the first report of implantation of absorbable metal stents in human use was in 2005. In a case of compassionate use to treat left pulmonary artery stenosis as a hybrid approach, an absorbable magnesium stent (AMS, Biotronik™, Germany) was implanted by Zartner and coworkers in a premature newborn. It showed only mild intimal proliferation with no stent-related inflammatory reaction. (Catheter Cardiovasc. Interv. 2007; 69:443-6; Catheter Cardiovasc Interv. 2005; 66:590-4. Schranz and coworkers demonstrated the use of the same stent for acute treatment of a newborn with severely impaired heart function due to a long-segment Re-CoA after complex surgical repair. In this patient, early restenosis was due to accelerated degradation. Catheter Cardiovasc. Interv. 2006; 67:671-3. Significant restenosis was observed 4 months after implanting a biodegradable magnesium stent within a stenotic aortopulmonary collateral in a 2-month-old girl with pulmonary atresia. Catheter Cardiovasc. Interv. 2007; 69:735-8.

The present invention is applicable to, but is not limited to, self-expandable stents, balloon-expandable stents, stent-grafts, and generally tubular medical devices in the treatment of CHD in infants and children. The present invention is further applicable to various stent designs including wire structures, and woven mesh structures.

Self expandable or self expanding stents include a bioabsorbable polymer scaffold that expands to the target diameter upon removal of an external constraint. The self expanding scaffold returns to a baseline configuration (diameter) when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be retracted by a mechanism that is available at the end of the catheter system and is operable by the physician. The self expanding bioabsorbable scaffold property is achieved by imposing only elastic deformation to the scaffold during the manufacturing step that compresses the scaffold into the sheath.

The bioabsorbable scaffold may also be expanded by a balloon. In this embodiment the scaffold is plastically deformed during the manufacturing process to tightly compress the scaffold onto a balloon counted on a catheter system. The scaffold is deployed at the treatment site by inflation of the balloon. The balloon will induce areas of plastic stress in the bioabsorbable material to cause the scaffold to achieve and maintain the appropriate diameter on deployment.

A stent scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are generally non-load bearing, serving to maintain connectivity between the rings. For example, a stent may include a scaffold composed of a pattern or network of interconnecting structural elements or struts.

Figure 1:
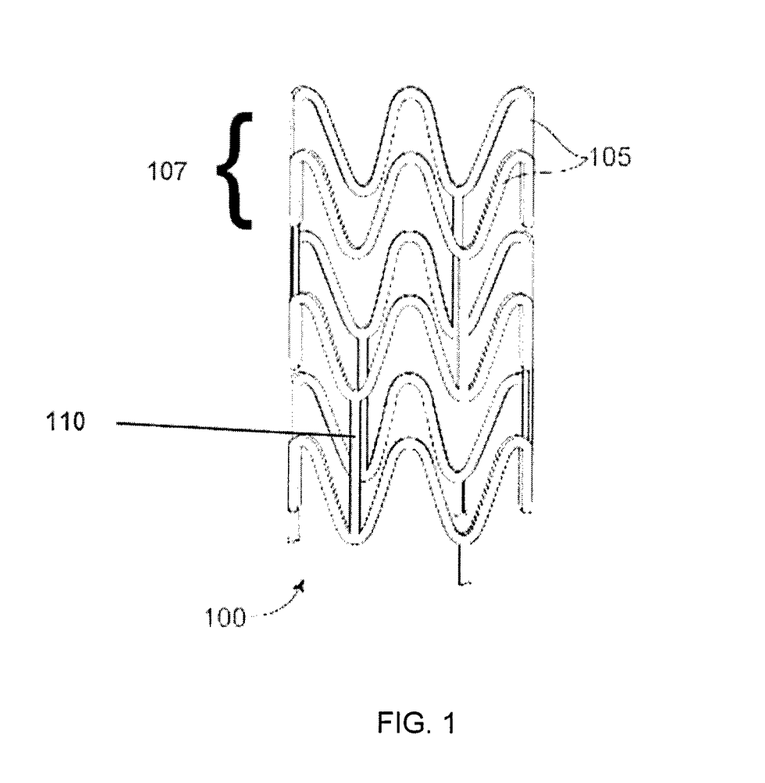
FIG. 1 depicts an exemplary stent scaffolding.

FIG. 1 depicts a view of an exemplary stent 100. In some embodiments, a stent may include a body, backbone, or scaffold having a pattern or network of interconnecting structural elements 105. Stent 100 may be formed from a tube (not shown). FIG. 1 illustrates features that are typical to many stent patterns including undulating sinusoidal cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to as a stent scaffold or scaffold. Although the scaffold may further include a coating, it is the scaffolding structure that is the load bearing structure that is responsible for supporting lumen walls once the scaffolding is expanded in a lumen.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

Alternatively, the scaffold design may be composed of radial bands that slide to increase the diameter of the scaffold. Such a design utilizes a locking mechanism to fix the stent at a target diameter and to achieve final radial strength. In other embodiments, the scaffold design could be braided polymer filaments or fibers.

Figure 2:
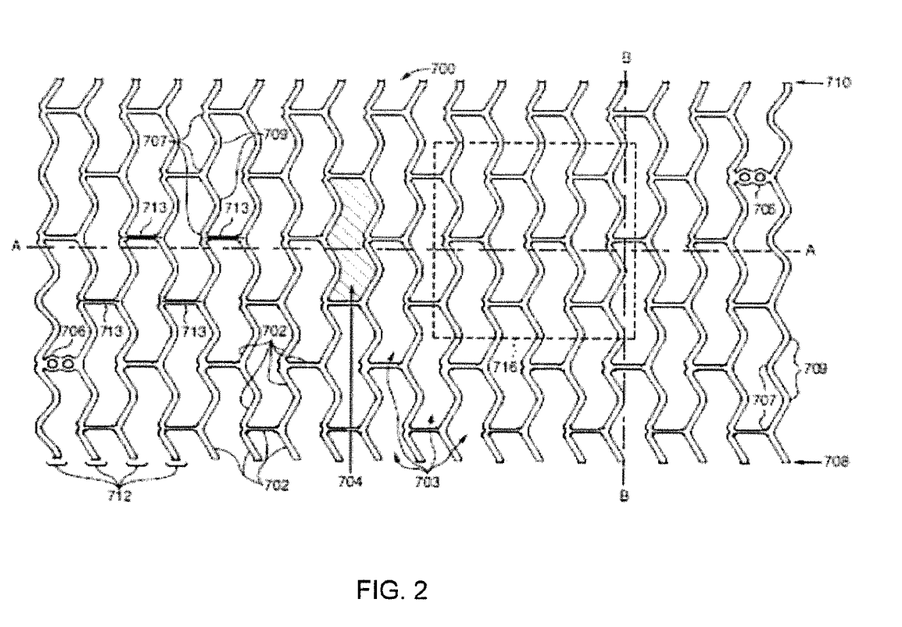
FIG. 2 depicts an exemplary stent pattern shown in a planar or flattened view.

In a preferred embodiment a stent scaffold has the stent pattern described in U.S. application Ser. No. 12/447,758 (US 2010/0004735) to Yang & Jow, et al. Other examples of stent patterns suitable for PLLA are found in US 2008/0275537. FIG. 2 depicts exemplary stent pattern 700 from US 2008/0275537. The stent pattern 700 is shown in a planar or flattened view for ease of illustration and clarity, although the stent pattern 700 on a stent actually extends around the stent so that line A-A is parallel or substantially parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at the same or substantially the same radial distance away from the central axis of the stent.

The stent pattern 700 includes various struts 702 oriented in different directions and gaps 703 between the struts. Each gap 703 and the struts 702 immediately surrounding the gap 703 define a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

Still referring to FIG. 2, the rings 712 are connected to each other by another group of struts that have individual lengthwise axes 713 parallel or substantially parallel to line A-A. The rings 712 are capable of being collapsed to a smaller diameter during crimping and expanded to their original diameter or to a larger diameter during deployment in a vessel. Specifically, pattern 700 includes a plurality of hinge elements 731, 732, 733, 734. When the diameter of a stent having stent patter 700 is reduced or crimped, the angles at the hinge elements decrease which allow the diameter to decrease. The decrease in the angles results in a decrease in the surface area of the gaps 703. Dimensions of the stent for pediatric applications depend upon such factors as the size of the anatomical lumen that is to be treated. In general, for most coronary and pulmonary applications, the diameter of the scaffold is 2 to 5 mm, or more narrowly 2.5 to 3.5 mm. In general, the length of the scaffold is 8 to 38 mm, or more narrowly, 8 to 12 mm, 12 to 18 mm, 18 mm to 38 mm. For some treatments, such as coarctation of the aorta in older children and peripheral pulmonary arteries, the scaffold diameter can be higher than 5 mm, for example 5 to 7 mm or 7 to 10 mm and the length can be greater than 38 mm, for example, 38 to 60 mm or 60 to 100 mm. All diameter ranges refer to inner or outer diameter and the as-fabricated or deployed diameter. The scaffolds for pediatric treatment have sufficient radial strength to support the vessels at a target diameter. The radial strength is a scaffold property and is a complex function of various factors such as scaffold material properties and stent geometry (e.g., strut dimensions, scaffold pattern). In general, for pediatric applications, scaffolds preferably have a radial strength of 200-900 mmHg. Scaffold design, scaffold material, morphology of scaffold material, or any combination thereof can be adjusted to account for different radial strength requirements for different congenital defects.

The prevailing mechanism of degradation of many bioabsorbable polymers is chemical hydrolysis of the hydrolytically unstable backbone. In a bulk degrading polymer, the polymer is chemically degraded throughout the entire polymer volume. As the polymer degrades, the molecular weight decreases. The reduction in molecular weight results in changes in mechanical properties (e.g., strength) and stent properties. For example, the strength of the scaffold material and the radial strength of the scaffold are maintained for a period of time followed by a gradual or abrupt decrease. The decrease in radial strength is followed by a loss of mechanical integrity and then erosion or mass loss. Mechanical integrity loss is demonstrated by cracking and by fragmentation. Enzymatic attack and metabolization of the fragments occurs, resulting in a rapid loss of polymer mass.

The bioabsorption properties include not only to the rate of chemical degradation of the scaffold material, but also the rate of loss of mechanical properties, in particular, the radial strength. Bioabsorption properties include the total resorption time, the time for the scaffold to absorb away completely from the implant site. Bioabsorption properties also include the time that radial strength is maintained. During this period the scaffold can support a lumen at an increased diameter.

Therefore, the behavior of a bioabsorbable stent upon implantation can divided into three stages of behavior. In stage I, the stent provides mechanical support. The radial strength is maintained during this phase. Also during this time, chemical degradation occurs which decreases the molecular weight. In stage II, the scaffold experiences a loss in strength and mechanical integrity. In stage III, significant mass loss occurs after hydrolytic chain scission yields water-soluble low molecular weight species.

The scaffold in the first stage provides the clinical need of providing mechanical support to maintain patency or keep a vessel open at or near the deployment diameter. In some treatments, the patency provided by the scaffold allows the stented segment of the vessel to undergo positive remodeling at the increased deployed diameter. Remodeling refers generally to structural changes in the vessel wall that enhances its load-bearing ability so that the vessel wall in the stented section can maintain an increased diameter in the absence of the stent support. A period of patency is required in order to obtain permanent positive remodeling.

In embodiments of the present invention, the bioresorption properties of scaffolds are adjusted for treatment of the specific CHD. The scaffold biodegradation properties such as the resorption time and the support time support are adjusted depending on the clinical need for various conditions. The support time may be dictated by one or more considerations, depending on the treatment, such as remodeling of the vessel, time needed for maturation of the patient's physiology, or both. A bioabsorbable polymer stent may be used to keep blood vessels open for a period of time, followed by resorption which allows the vessel to grow to normal size, without the restrictions of a permanent metallic stent.

The manufacturing process of a bioabsorbable scaffold includes selection of a bioabsorbable polymer raw material or resin. Detailed discussion of the manufacturing process of a bioabsorbable stent can be found elsewhere, e.g., U.S. Patent Publication No. 20070283552. The fabrication methods of a bioabsorbable stent can include the following steps:

(1) forming a polymeric tube from a biodegradable polymer resin using extrusion, (2) radially deforming the formed tube to increase radial strength, (3) forming a stent scaffolding from the deformed tube by laser machining a stent pattern in the deformed tube with laser cutting, in exemplary embodiments, the strut thickness can be 100-200 microns, or more narrowly, 120-180, 130-170, or 140-160 microns, (4) optionally forming a therapeutic coating over the scaffolding, (5) crimping the stent over a delivery balloon, and (6) sterilization with election-beam (E-beam) radiation.

Poly(L-lactide) (PLLA) is attractive as a stent material due to its relatively high strength and rigidity at human body temperature, about 37° C. Since it has a glass transition temperature between about 60 and 65° C. (Medical Plastics and Biomaterials Magazine, March 1998), it remains stiff and rigid at human body temperature. This property facilitates the ability of a PLLA stent scaffold to maintain a lumen at or near a deployed diameter without significant recoil (e.g., less than 10%). In general, the Tg of a semicrystalline polymer can depend on its morphology, and thus how it has been processed. Therefore, Tg refers to the Tg at its relevant state, e.g., Tg of a PLLA resin, extruded tube, expanded tube, and scaffold.

Additional exemplary biodegradable polymers for use with a bioabsorbable polymer scaffolding include poly(D-lactide) (PDLA), polymandelide (PM), polyglycolide (PGA), poly(L-lactide-co-D,L-lactide) (PLDLA), poly(D,L-lactide) (PDLLA), poly(D,L-lactide-co-glycolide) (PLGA) and poly (L-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

Polymers that are more flexible or that have a lower modulus than those mentioned above may also be used. Exemplary lower modulus bioabsorbable polymers include, polycaprolactone (PCL), poly(trimethylene carbonate) (PTMC), polydioxanone (PDO), poly(4-hydroxy butyrate) (PHB), and poly (butylene succinate) (PBS), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) or poly(L-lactide)-co-polycaprolactone (PLLA-co-PCL). The composition of the blend can include 1-5 wt % of low modulus polymer.

As indicated above, the radial strength of the finished stent product (at time of implantation before bioresorption begins) depends on factors such as scaffold material properties and stent geometry. It has been found that radial strength depends on the initial molecular weight or molecular weight at the time of implantation (e.g., Mn(time=0) or Mn(0)). For a given set of factors other than Mn(0), Mn(0) may be adjusted to provide a radial strength that will support a lumen at a target diameter, for example, a radial strength of at least 200 mmHg.

It has been found that the scaffold biodegradation properties, the resorption time and the support time also depend on the Mn(0) of the scaffold. Mn(0) can be adjusted to provide desired resorption time and support time. It has also been found that the monomer content of the bioabsorbable scaffold material can be adjusted to provide desired resorption time and support time. Specifically, it has been shown that the degradation profile of poly(L-lactide) is strongly dependent on Mn(0) and the degradation rate constant of PLLA, U.S. patent application Ser. No. 13/104,732.

Studies showed that the degradation rate constant of PLLA is strongly dependent on the L-lactide (LLA) monomer content. The hydrolytic degradation of a PLLA scaffold increases with an increase in LLA monomer content. As a result, the Mn and radial strength as a function of time also depend on LLA monomer content. Increasing Mn(0) at implantation increases the support time and the resorption time, while decreasing the Mn(0) has the opposite effect. Increasing the monomer content accelerates the decrease in Mn, thus decreasing support time and resorption time. Increasing the monomer content slows down the decrease in Mn, thus increasing support time and resorption time.

Therefore, the Mn(0), monomer content, or both of the bioabsorbable polymer scaffold can be adjusted to obtain a support time of at least 3, at least 6 months, 1-3 months, 2-3 months, 3 to 6 months. The Mn(0), monomer content, or both of the bioabsorbable scaffold can be adjusted to maintain a radial strength of at least 200 mmHg, at least 400 mmHg, at least 600 mmHg, 200 to 400 mmHg, or 200 to 600 mmHg.

An exemplary PLLA scaffold may have an initial L-lactide monomer content within the range of less than 0.02 wt %, 0.02 to 0.2 wt %, and 0.02 wt % to 1 wt %, or any sub range or value in these ranges. The Mn(0) can be at least 60 kDa, 60 to 66 kDa, 66 to 80 kDa, 80 to 120 kDa, greater than 120 kDa, or any sub-range or value in these ranges. An exemplary PLLA scaffold can have any combination of these Mn(0) and L-lactide monomer content.

The term "molecular weight" can refer to one or more definitions of molecular weight. "Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. Molecular weight is typically expressed in grams/mole which is referred to as "Daltons." It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi. Unless otherwise specified, "molecular weight" will refer to number average molecular weight (Mn).

Embodiments of the present invention include methods of treating peripheral pulmonary stenosis in a human patient with a bioabsorbable polymer scaffold. As indicated above, peripheral pulmonary stenosis is congenital stenosis of the pulmonary artery branches. Such branches exhibit narrowed segments of one or more of the main or peripheral branches of the pulmonary artery. The pulmonary branches include the branches of the main pulmonary artery, and then second and third order branches that feed the more peripheral areas of the lung.

The method includes identifying segments in one or more peripheral branches of the pulmonary artery of the patient that are narrowed. Narrowed segments are identified by pulmonary angiography. Segments are characterized as narrowed on the basis of clinical examination and angiographic findings of narrowed vessels in the peripheral areas of the lung. A peripheral branch can have one or more narrowed segments. Narrowed segments can be variable in length, and are usually multiple, requiring 2-10 stents, of lengths 6 to 40 mm depending on the location of the artery and age of the child.

The method further includes deploying bioabsorbable polymer scaffolds in one or more of the narrowed segments in the one or more peripheral branches. In some embodiments, more than one scaffold is implanted in a branch. The deployed bioabsorbable scaffolds provide supports in the segment at an increased diameter to allow increased blood flow. This increased blood flow facilitates development of the lungs of the human patient. The number of scaffolds deployed can be 2 to 5, 5 to 10, or 10 or more. The age of the human patient at the time of deployment can be 1 to 3 years, less than 12 months, newborn to 1 month, 1 to 3 months, 3 to 6 months, or 6 to 12 months.

One or more of the scaffolds maintain support of the segments for a period of at least 3, at least 5, at least 6, at least 8, at least 12, 1 to 3, 3 to 6, 6 to 12, or greater than 12 months. The support time of the scaffold can correspond to a time determined to be necessary for adequate development of lungs. The support time may also correspond to a time necessary to achieve remodeling of a segment.

In some embodiments, the scaffolds deployed in the one or more peripheral branches completely absorb away in less than 1 year, less than 2 years, between 1 to 2 years, between 1.5 to 2 years, between 2 to 2.5 years, or greater than 2.5 years. The support time and the absorption time of a scaffold can be adjusted through initial molecular weight of the scaffold material, monomer content of the scaffold material, or both. For example, the scaffold material is PLLA and the LLA monomer content is adjusted.

The target diameter range of the deployed scaffolds, which can correspond, but not necessarily, to the diameter of the scaffolds as fabricated before crimping, can be between 2 and 8 mm, or more narrowly 2 to 5 mm. The target diameter can be based on a diameter that can be determined or is known to provide normal lung development in a healthy subject. In some embodiments, the target diameter can be the same for all deployed scaffolds. In other embodiments, the target diameters can be different for different scaffolds. In such embodiments, the target diameters of the scaffolds are tailored to a desired size that facilitates the treatment. For example, the scaffolds have sizes that are based on what is known to provide normal lung development in a healthy subject.

The length of the scaffolds can be between 4 and 40. In some embodiments, the length of the scaffolds is the same in each segment. In other embodiments, the length of the scaffolds can be different in different segments. In such embodiments, the length of the scaffold can be tailored to the length of the narrowed segment.

In further embodiments, the support time for each scaffold is the same. In other embodiments, the support time for the scaffolds can be different in different segments.

The method of treatment may further include implanting at least one additional bioabsorbable scaffold at the site of deployment of at least one of the scaffolds after it has partially or completely absorbed. The additional scaffold may be deployed at a greater diameter than the initial scaffold to accommodate for growth in the pulmonary branch.

In further embodiments, the method can include performing surgical repair in the heart 1 to 2 years after implantation. In such embodiments, the surgical repair may be performed after all of the scaffolds have completely absorbed. In other embodiments, the surgical report is performed prior to absorption of at least some of the scaffolds.

Embodiments of the present invention include a method of treating Tetralogy of the Fallot in a human patient. The method includes identifying a human patient less than 12 months of age having abnormalities associated with Tetralogy of the Fallot. The abnormalities include pulmonary stenosis and at least two additional abnormalities from the group consisting of ventricular septal defect, right ventricular hypertrophy, and overriding of the aorta. The method includes deploying a bioabsorbable polymer scaffold in a narrowed segment of the pulmonary artery of the patient. The deployed bioabsorbable polymer scaffold provides support at the segment at an increased diameter to allow increased blood flow into the heart of the patient. This increased blood flow facilitates development of the lungs prior to repair of the abnormalities. The chance of survival is increased and success of surgery to correct the abnormalities is increased.

The deployment of the scaffold may take place when the patient has an age of less than 1 month old, 1 to 3 months, 3 to 6 months, 6-9 months, or 9 to 12 months. The method further includes performing surgical repair of at least one of the additional abnormalities at some time after deployment of the scaffold. The surgical repair can take place 1 to 12 months or greater than 12 months after deployment of the scaffold. In some embodiments, the surgical repair is performed during the support time of the scaffold. The surgery can be performed prior to or after complete resorption of the scaffold. The surgery may be performed after the support time, but prior to complete resorption of the scaffold.

The scaffold maintains support of the segment for a period of at least 3, 5, 6, 8, 12, or greater than 12 months. The support time can correspond to a time determined to be necessary for adequate development of lungs. The support time may also correspond to a time necessary to achieve remodeling of a segment.

The method further includes implanting an additional bioabsorbable scaffold at the implant site of the scaffold after the scaffold has partially or completely absorbed. The additional scaffold may be deployed at a greater diameter than the absorbed scaffold to accommodate for growth in the pulmonary artery.

In some embodiments, the scaffold completely absorbs away in less than 1 year, less than 2 years, between 1 to 2 years, between 1.5 to 2 years, between 2 to 2.5 years, or greater than 2.5 years. The support time and the resorption time of the scaffold can be adjusted through initial molecular weight, monomer content, or both.

Embodiments of present invention include methods of treatment including maintaining patency of the ductus arteriosus for a period of time after birth of a patient as a palliative measure. In such embodiments, a newborn human patient less than a month of age have be identified as having a complex congenital cardiac malformation. Such malformations can include single ventricle with pulmonary atresia, hypoplastic left-heart syndrome and transposition of great vessels.

The method includes deploying a bioabsorbable polymer scaffold in the ductus arteriosis of the patient to maintain patency of the ductus arteriosus. Maintaining the patency of the ductus arteriosis allows blood flow to the lungs and the body until the complex congenital cardiac malformation is repaired. The deployed bioabsorbable scaffold provides support to the ductus arteriosis at an increased diameter to allow increased blood flow into the heart and body of the patient.

The deployment of the scaffold may take place when the patient is less than 1 month old. The method further includes performing surgical repair of at least one of the malformations at some time after deployment of the scaffold. The surgical repair can take place 1 to 12 months or greater than 12 months after deployment of the scaffold. In some embodiments, the surgical repair can be performed during the support time of the scaffold. The surgery can be performed prior to or after complete resorption of the scaffold. The surgery may be performed after the support time, but prior to complete resorption of the scaffold.

The scaffold maintains support of the ductus arteriosis for a period of at least 3, 5, 6, 8, 12, or greater than 12 months. The support time can correspond to a time determined to be necessary for adequate development of the heart lungs prior to the corrective surgery.

In some embodiments, the scaffold completely absorbs away in less than 1 year, less than 2 years, between 1 to 2 years, between 1.5 to 2 years, between 2 to 2.5 years, or greater than 2.5 years. The support time and the resorption time of the scaffold can be adjusted through initial molecular weight, monomer content, or both.

One scaffold may not provide patency for a sufficient time. Additionally, the growth of the ductus arteriosis may require dilation of the ductus arteriosis to a larger diameter. To address such situations, embodiments can include implanting another bioabsorbable scaffold in the ductus arteriosis after the first scaffold implanted has partially or completely absorbed.

Further embodiments include treating coarctation of the aorta in a human patient with a bioabsorbable polymer scaffold. The method includes identifying a narrowed segment in the aorta of a human patient that is less than 12 months of age. The narrowed segment is in an area where the ductus arteriosus inserts in the aorta. The narrowed segment may be proximal to the ductus arteriosus, at the insertion of the ductus arteriosus, or distal to the insertion of the ductus arteriosus.

The method includes deploying a bioabsorbable polymer scaffold at the narrowed segment. The bioabsorbable scaffold provides support at the segment at an increased diameter. The scaffold can maintain a radial strength of at least 200 mmHg for at least 6 months and maintain the support of the segment.

In the present invention, growth of the patient is accommodated since the scaffold absorbs away from the implant site. The method can include implanting an additional bioabsorbable scaffold at the site of deployment of the scaffold after it has partially or completely absorbed. The additional scaffold may be deployed at a greater diameter than the absorbed scaffold to accommodate growth in the aorta. Restenosis can be addressed by incorporating an antiproliferative agent in or on the scaffold to reduce or control hyperplasia at the implant site.

The scaffolds used in the treatments discussed herein may include to therapeutic agents, such as antiproliferative The scaffolds used in the treatments discussed herein may be coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin II, actinomycin XI, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic anti-thrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

In some embodiments, the scaffolds can include a prohealing material. The prohealing material can be dispersed within a bioabsorbable polymer. A prohealing material refers to a material that has the property that it promotes or enhances re-endothelialization of arterial lumen to promote healing of the vascular tissue. The prohealing-containing portions of the scaffold can attract, bind and eventually become encapsulated by endothelial cells. In certain embodiments, the prohealing-containing portions of the stent attract, bind, and become encapsulated by endothelial progenitor cells. The attraction, binding, and encapsulation of the cells will reduce or prevent the formation of emboli or thrombi due to the loss of the mechanical properties that could occur if the scaffold was insufficiently encapsulated. In some embodiments, the enhanced re-endothelialization promotes the endothelialization at a rate faster than the loss of mechanical properties of the scaffold.

In some embodiments, the prohealing material can be dispersed in the body of the bioabsorbable polymer substrate or scaffold. The prohealing material can also be dispersed within a bioabsorbable polymer coating over a surface of a scaffold.

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing material can be an endothelial cell (EDC) binding agent. In some embodiments, the EDC binding agent can be protein, peptide and antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways (see, e.g., Martin, S. M., et al., J. Biomed. Mater. Res. 70A:10-19 (2004)). Endothelial cells can be selectively targeted (for the targeted delivery of immunoliposomes) using scFv A5 (Volkel, T., et al., Biochimica et Biophysica Acta 1663:158-166 (2004)). Junction membrane protein vascular endothelial (VE)-cadherin has been shown to bind to endothelial cells and down regulate apoptosis of the endothelial cells (Spagnuolo, R., et al., Blood 103:3005-3012 (2004)).

In some embodiments, the EDC binding agent can be the active fragment of osteopontin, (Val-Asp-Val-Pro-Asp-Gly-Arg-Gly-Asp-Ser-Leu-Ala-Tyr-Gly (SEQ ID NO:1)). Other useful EDC binding agents include EPC (epithelial cell) antibodies, RGD peptide sequences, RGD mimetics, and combinations thereof.

The EDC binding protein and peptide can be prepared according to the established methods, e.g., isolation and purification from natural sources, recombinant techniques, or combinatorial chemistry for the synthesis of peptides. For example, the active fragment of osteopontin can be readily prepared by combinatorial synthesis using, e.g., solid-phase peptide sequencing (e.g., a Merrifield synthesis). The scFv A5 protein can be synthesized by gene expression as described in the literature from the HisCysForNot(5'-TAG TGC GGC CGC TTA GCA TGC TCC GCC ATG GTG ATG GTG ATG ATG CGC ACG TTT GAT TTC CAG TTT GGT-3' (SEQ ID NO:2)) (Volkel, T., et al., Biochimica et Biophysica Acta 1663:158-166 (2004)).

In further embodiments, the prohealing material may a substance or agent that attracts and binds endothelial progenitor cells. Representative substances or agents that attract and bind endothelial progenitor cells include antibodies such as CD-34, CD-133, and vegf type 2 receptor. An agent that attracts and binds endothelial progenitor cells can include a polymer having nitric oxide donor groups.

In other embodiments, the EDC binding agent can be chemically linked to a polymer (e.g., via a linkage). The polymer can be the polymer of the coating or a polymer from which the device is made. For example, the active fragment of osteopontin can be attached to the acid terminal poly(lactic acid) via a PEG linkage.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a coarctation of the aorta in a human patient comprising:
   identifying a narrowed segment in the aorta of a human child who is born with a coarctation of the aorta, wherein the aorta narrows in an area where the ductus arteriosus inserts in the aorta;
   deploying a bioabsorbable polymer scaffold at the narrowed segment;
   wherein the deployed bioabsorbable polymer scaffold provides support at the segment at an increased diameter;
   wherein the deployed bioabsorbable polymer scaffold eventually completely absorbs away;
   wherein the bioabsorbable polymer scaffold comprises poly(L-lactide) (PLLA), wherein the PLLA has an initial molecular weight (Mn(0)) of at least 60 kDa, 60 to 66 kDa, 66 to 80 kDa, 80 to 120 kDa, or greater than 120 kDa and an initial L-lactide monomer content within the range less than 0.02 wt %, 0.02 wt % to 0.2 wt %, or 0.02 wt % to 1 wt %; or the bioabsorbable polymer scaffold comprises, poly(L-lactide) (PLLA) or poly(L-lactide-co-glycolide) (PLLGA), in combination with a lower modulus polymer selected from the group consisting of polycaprolactone (PCL), poly(trimethylene carbonate) (PTMC), polydioxanone (PDO), poly(4-hydroxy butyrate) (PHB), poly(butylene succinate) (PBS), poly (L-lactide)-co-polycaprolactone (PLLA-co-PCL), poly (L-lactide)-b-polycaprolactone (PLLA-b-PCL), and blends and copolymers thereof;
   wherein the deployed bioabsorbable polymer scaffold maintains a radial strength of at least 200 mm Hg for at least 6 months.

2. The method of claim 1, wherein the narrowed segment is proximal to the ductus arteriosus.

3. The method of claim 1, wherein the narrowed segment is at the insertion of the ductus arteriosus.

4. The method of claim 1, wherein the narrowed segment is distal to the insertion of the ductus arteriosus.

5. The method of claim 1, wherein prior to deployment, the scaffold is constrained at a reduced diameter by a sheath and is deployed by removing the sheath and allowing the scaffold to self-expand to the increased diameter.

6. The method of claim 1, wherein prior to deployment, the scaffold is constrained at a reduced diameter around a balloon and is deployed by expanding the balloon which expands the scaffold to the increased diameter.

7. The method of claim 1, further comprising implanting an additional bioabsorbable polymer scaffold at the site of deployment of the scaffold after it has partially or completely absorbed, wherein the additional scaffold is deployed at a greater diameter than the absorbed scaffold to accommodate for growth in the aorta.

8. The method of claim 1, wherein the scaffold comprises an antiproliferative agent to reduce hyperplasia and stenosis in the segment.

9. The method of claim 1, wherein the bioabsorbable polymer scaffold comprises poly(L-lactide) (PLLA), wherein the PLLA has an initial molecular weight (Mn(0)) of 60 to 66 kDa, 66 to 80 kDa, or 80 to 120 kDa, and an initial L-lactide monomer content within the range less than 0.02 wt %, 0.02 wt % to 0.2 wt %, or 0.02 wt % to 1 wt %.

10. The method of claim 1, wherein the bioabsorbable polymer scaffold comprises, poly(L-lactide) (PLLA) or poly(L-lactide-co-glycolide) (PLLGA), in combination with a low modulus polymer selected from the group consisting of polycaprolactone (PCL), poly(trimethylene carbonate) (PTMC), polydioxanone (PDO), poly(4-hydroxy butyrate) (PHB), poly(butylene succinate) (PBS), poly(L-lactide)-co-polycaprolactone (PLLA-co-PCL), poly(L-lactide)-b-polycaprolactone (PLLA-b-PCL), and blends and copolymers thereof.

* * * * *

SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Active fragment of osteopontin

<400> SEQUENCE: 1

Val Asp Val Pro Asp Gly Arg Gly Asp Ser Leu Ala Tyr Gly
1               5                   10

<210> SEQ ID NO 2
<211> LENGTH: 69
<212> TYPE: DNA
<213> ORGANISM: Artificial Sequence
<220> FEATURE:
<223> OTHER INFORMATION: Primer

<400> SEQUENCE: 2
tagtgcggcc gcttagcatg ctccgccatg gtgatggtga tgatgcgcac gtttgatttc    60
cagtttggt                                                            69